(12) United States Patent
Jagelski et al.

(10) Patent No.: US 10,478,208 B2
(45) Date of Patent: Nov. 19, 2019

(54) ENDOSCOPIC SUBMUCOSAL DISSECTION HOOD

(71) Applicant: Boston Scientific Scimed, Inc., Maple Grove, MN (US)

(72) Inventors: Matthew Robert Jagelski, West Roxbury, MA (US); Shawn Ryan, Upton, MA (US); Celine Mee Ling Chin, Brookline, MA (US); Norman C. May, Northborough, MA (US); Catherine Shimin Yee, Randolph, MA (US); Paul Smith, Smithfield, RI (US); Ray Tong, Foxboro, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 142 days.

(21) Appl. No.: 15/332,433

(22) Filed: Oct. 24, 2016

(65) Prior Publication Data

US 2017/0112523 A1    Apr. 27, 2017

Related U.S. Application Data

(60) Provisional application No. 62/245,472, filed on Oct. 23, 2015.

(51) Int. Cl.
| | | |
|---|---|---|
| *A61B 1/04* | (2006.01) | |
| *A61B 17/32* | (2006.01) | |
| *A61B 1/00* | (2006.01) | |
| *A61B 17/00* | (2006.01) | |
| *A61N 7/00* | (2006.01) | |
| *A61B 17/29* | (2006.01) | |
| *A61B 18/02* | (2006.01) | |
| *A61B 18/14* | (2006.01) | |
| *A61B 18/00* | (2006.01) | |

(52) U.S. Cl.
CPC .... *A61B 17/320016* (2013.01); *A61B 1/0014* (2013.01); *A61B 1/00087* (2013.01); *A61B 1/00089* (2013.01); *A61B 1/00101* (2013.01); *A61B 17/00234* (2013.01); *A61B 17/29* (2013.01); *A61B 18/02* (2013.01); *A61B 18/1492* (2013.01); *A61N 7/00* (2013.01); *A61B 2017/00269* (2013.01); *A61B 2017/00296* (2013.01); *A61B 2017/00331* (2013.01); *A61B 2018/00601* (2013.01); *A61B 2018/00982* (2013.01); *A61B 2018/0212* (2013.01); *A61B 2018/1412* (2013.01); *A61N 2007/0043* (2013.01)

(58) Field of Classification Search
CPC ............ A61B 1/00087; A61B 1/00089; A61B 17/32056; A61B 17/320016
USPC .......... 606/113, 114, 139–148; 600/127, 129
See application file for complete search history.

(56) References Cited

U.S. PATENT DOCUMENTS 4,742,817 A * 5/1988 Kawashima ......... A61B 1/0052
                                                         600/104
5,047,848 A * 9/1991 Krauter ................ A61B 1/0008
                                                          33/501

(Continued)

*Primary Examiner* — Matthew J Kasztejna (57) ABSTRACT

The present disclosure relates to the field of endoscopy. In particular, the present disclosure relates to systems and methods suitable for resecting or dissecting large areas of mucosal or submucosal tissue. The system may apply tension to and continuously manipulate mucosal tissue such that large lesions may be resected or dissected by a cutting element disposed at the distal end of an endoscope.

20 Claims, 7 Drawing Sheets

(56) References Cited

U.S. PATENT DOCUMENTS

| | | | | |
|---|---|---|---|---|
| 5,624,379 | A * | 4/1997 | Ganz | A61B 10/06 600/104 |
| 5,993,447 | A * | 11/1999 | Blewett | A61B 18/1477 600/105 |
| 6,071,233 | A * | 6/2000 | Ishikawa | A61B 1/0014 600/104 |
| 6,358,197 | B1 * | 3/2002 | Silverman | A61F 2/04 600/29 |
| 6,689,130 | B2 * | 2/2004 | Arai | A61B 18/1492 600/104 |
| 7,566,300 | B2 * | 7/2009 | Devierre | A61B 1/00087 600/104 |
| 7,918,783 | B2 * | 4/2011 | Maseda | A61B 1/018 600/104 |
| 8,075,478 | B2 * | 12/2011 | Campos | A61B 1/0008 600/111 |
| 8,226,544 | B2 * | 7/2012 | Muyari | A61B 18/1492 600/104 |
| 8,602,970 | B2 * | 12/2013 | Muyari | A61B 1/00087 600/104 |
| 2001/0053909 | A1 | 12/2001 | Nakada et al. | |
| 2004/0172018 | A1 * | 9/2004 | Okada | A61B 18/1402 606/46 |
| 2004/0249239 | A1 | 12/2004 | Silverman et al. | |
| 2009/0043154 | A1 | 2/2009 | Okada | |
| 2013/0331855 | A1 | 12/2013 | Smith et al. | |
| 2014/0066707 | A1 | 3/2014 | Muyari et al. | |
| 2014/0288584 | A1 | 9/2014 | De La Mora Levy et al. | |

* cited by examiner

ENDOSCOPIC SUBMUCOSAL DISSECTION HOOD

PRIORITY

This application claims the benefit of priority under 35 U.S.C. § 119 to U.S. Provisional Patent Application Ser. No. 62/245,472, filed Oct. 23, 2015, which is incorporated by reference in its entirety and for all purposes.

FIELD

The present disclosure relates to the field of endoscopy. Specifically, the present disclosure relates to systems and methods useful for endoscopic submucosal dissection (ESD) and/or endoscopic mucosal resection (EMR). More specifically, the present disclosure relates to an endoscopic hood that provides enhanced visualization of the working area within which tissue engaging and tissue cutting elements operate to dissect or resect mucosal and submucosal lesions.

BACKGROUND

Physicians have become increasingly willing to perform interventional and therapeutic endoscopic procedures including, for example, full thickness removal of large tissue lesions such as cancer, tunneling under the mucosal layer of the gastrointestinal (GI) tract or respiratory system to treat submucosal tissues, repair of post-surgical complications (e.g., post-surgical leaks, breakdowns of surgical staple lines and/or anastomotic leaks), thoracic surgery and airway/pleural space procedures. Specialized tools may be used to allow the physician to perform these complex procedures faster and easier. A common way to incorporate these specialized tools onto the distal end of the endoscope is through the use of endoscopic hoods or caps. The fully circumferential design of currently available endoscopic hoods tends to hinder visualization of the target tissue and provide little working space for multiple tools to operate simultaneously. Although double-channel endoscopes may be available at some medical facilities, the individually articulating tools within each channel tend to be ergonomically difficult to control, especially by a single physician.

SUMMARY

The present disclosure provides a high-visibility endoscope hood that allows the medical professional to manipulate mucosal tissue such that the entire submucosal lesion is exposed for removal.

In one aspect, the present disclosure relates to an endoscopic system comprising: 1) an endoscope comprising an elongate body having a proximal end and a distal end and a working channel disposed within the elongate body; 2) an endoscopic hood coupled to the distal end of the endoscope, the endoscopic hood comprising: a first portion that comprises a proximal end, a distal end, and first and second lumens extending therebetween, wherein the first lumen is in open communication with the working channel of the endoscope; and a second portion extending from the distal end of the first portion, said second portion comprising a wall and defining a working area adjacent a surface of the wall and the first lumen; 3) a first shaft having a proximal end and a distal end disposed within the working channel and the first lumen; and 4) a second shaft having a proximal end and a distal end disposed alongside the elongate body and extending through the second lumen. The wall may include a curved wall and the working area may be adjacent to a concave surface of the curved wall and the first lumen. The curved wall may include a variety of shapes, including, for example, a partial hollow conic section, a partial hollow cylinder or a partial hollow sphere. A cross-section of the wall may be in the form of an arc ranging from approximately 90 degrees to approximately 180 degrees. The wall may be formed from a transparent material. The endoscopic system may further comprise a support member extending into the first lumen. The support member may define an aperture having a non-circular cross-section configured to slidably receive the first shaft. The first shaft may be slidably, but not rotationally, disposed within the working channel, first lumen and aperture. The distal end of the first shaft may include a shape memory material configured to assume a bent configuration when unconstrained by an over-sheath or core wire. In addition, or alternatively, the distal end of the first shaft may be configured to bend upon actuation by an operation. The distal end of the first shaft may further include a tissue cutting element. The second shaft may be slidably and rotationally disposed within the second lumen. The distal end of the second shaft may include a tissue engaging element. Rotating a proximal end of the second shaft in a first direction may move the tissue engaging element towards the working area, and rotating a proximal end of the second shaft in a second direction may move the tissue engaging element away from the working area.

In another aspect, the present disclosure relates to an endoscopic hood configured to be disposed at a distal end of an endoscope comprising an endoscope body and a working channel disposed within the endoscope body, the endoscopic hood comprising: 1) a first portion that comprises a proximal end, a distal end, and first and second lumens extending therebetween; and 2) a second portion extending from the distal end of the first portion, said second portion comprising a wall and defining a working area adjacent the wall and the first lumen, wherein the first lumen is configured to receive a shaft of a first device disposed in the working channel of the endoscope, and wherein the second lumen is configured to receive a shaft of a second device disposed alongside an elongate body of the endoscope. The wall may include a curved wall and the working area may be adjacent to a concave surface of the curved wall and the first lumen. The curved wall may include a variety of shapes, including, for example, a partial hollow conic section, a partial hollow cylinder or a partial hollow sphere. A cross-section of the wall may be in the form of an arc ranging from approximately 90 degrees to approximately 180 degrees. The wall may formed from a transparent material. The endoscopic hood may further comprise a support member extending into the first lumen. The support member may define an aperture having a non-circular cross-section.

In another aspect, the present disclosure relates to a method of resecting or dissecting tissue comprising inserting the endoscopic system into a body lumen of a patient, positioning the endoscopic hood of the endoscopic system over the surface of a target tissue, and resecting or dissecting the target tissue with the tissue cutting element while engaging the tissue with the tissue engaging element.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

It is noted that the drawings are intended to depict only typical or exemplary embodiments of the disclosure. It is further noted that the drawings may not be necessarily to scale. Accordingly, the drawings should not be considered as limiting the scope of the disclosure. The disclosure will now be described in greater detail with reference to the accompanying drawings.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to an endoscope hood attached to the distal end of an endoscope, it should be appreciated that the endoscope hood disclosed herein may be attached to a variety of medical devices that are inserted into a lumen of a patient, including for example, guide lumens, ports, optical wands and the like. As used herein, the term "distal" refers to the end farthest away from a medical professional when introducing a device into a patient, while the term "proximal" refers to the end closest to the medical professional when introducing a device into a patient.

Figure 1:
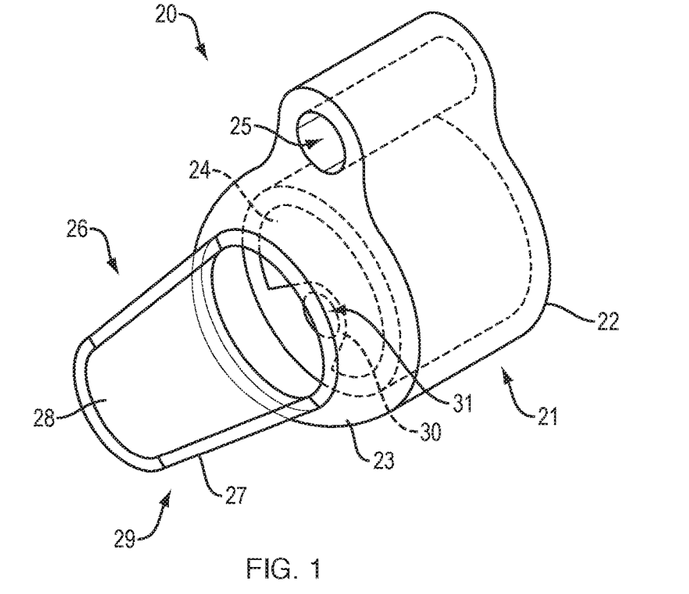
FIG. 1 provides a perspective view of an endoscopic hood, according to an embodiment of the present disclosure.
Figure 2:
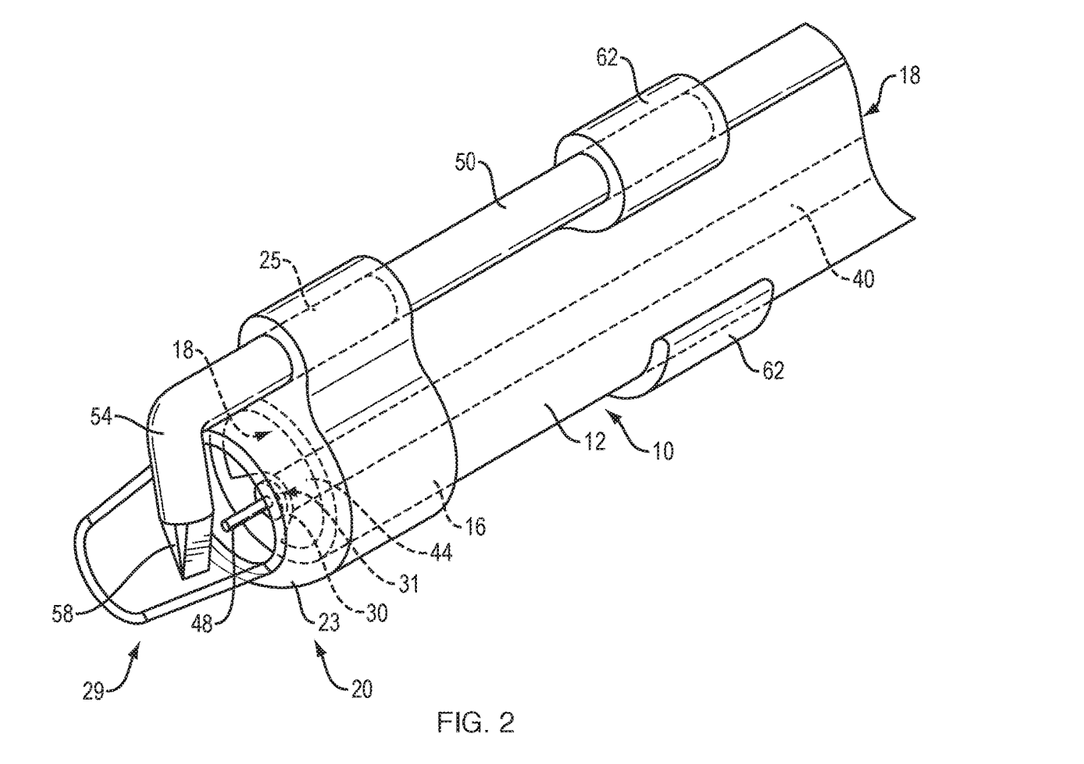
FIG. 2 provides a perspective view of the endoscopic hood of FIG. 1 attached to the distal end of an endoscope in a delivery configuration according to an embodiment of the present disclosure.

In one embodiment, the present disclosure provides a system for performing interventional and therapeutic procedures including, but not limited to, removal of large lesions such as cancer, tunneling under the mucosal layer of the GI or respiratory tract to treat submucosal tissues and endoscopic repair of post-surgical complications such as post-surgical leaks, breakdowns of surgical staple lines and/or anastomotic leaks. As illustrated in FIG. 1, in one embodiment the present disclosure includes an endoscopic hood 20 comprising a first portion 21 with a proximal end 22, a distal end 23, and first 24 and second 25 lumens extending therebetween. The first lumen 24 is configured to receive a first shaft 40, and the second lumen 25 is configured to receive a second shaft 50 (FIG. 2). The endoscopic hood 20 further includes a second portion 26 extending from the distal end 23 of the first portion 21. The second portion 26 may include a wall 27 that defines a working area 29 adjacent to the wall 27 and first lumen 24. The wall 27 may include a curvature that defines a concave inner surface 28. For example, the concave inner surface 28 may include one or more of a partially hollow conic section, a partially hollow cylinder or a partially hollow sphere, among other configurations. A cross-section of the wall 27 may form an arc that ranges from approximately 90 degrees to approximately 180 degrees. The wall may be formed from a transparent or translucent material, such as a clear polymer-based material (i.e., clear plastics, etc.) as are known in the art. Still referring to FIG. 1, a support member 30 may extend into the first lumen 24 at the distal end 23 of the first portion 21. The support member 30 may define an aperture 31 that includes a non-circular cross-section configured to receive the distal end 44 of first shaft 40 (FIG. 2).

Figure 7:
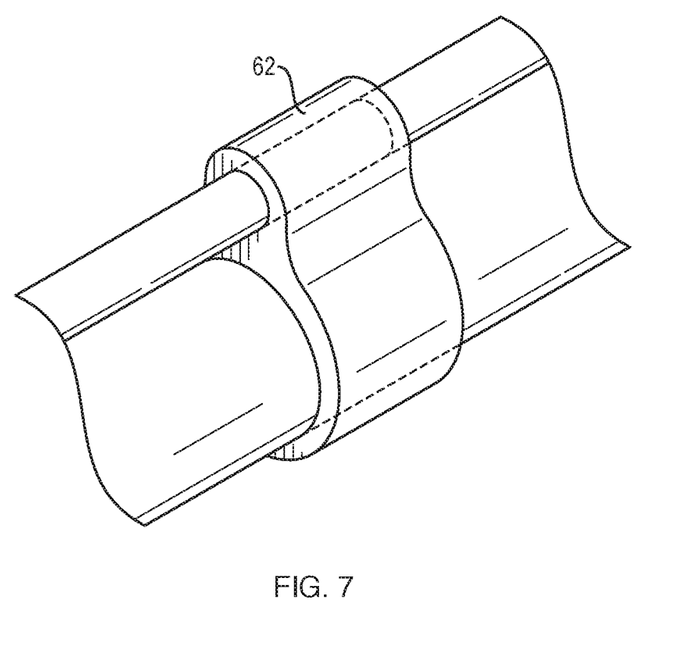
FIG. 7 provides schematic partial perspective view of an alternative design for the clip depicted in FIG. 2 attached to an endoscope, according to an embodiment of the present disclosure.

Referring to FIG. 2, in an embodiment the present disclosure includes an endoscopic system that includes an endoscope 10 coupled to the distal end 23 of the endoscopic hood 20 of FIG. 1. The endoscope 10 may include an elongate body 12 having a proximal end (not shown), a distal end 16 and a working channel 18 extending therethrough. A first shaft 40 comprising a proximal end (not shown) and distal end 44 is disposed within the working channel 18 of endoscope 10. The distal end 44 of first shaft 40 is supported by, and slidably disposed within, the aperture 31 of support member 30. A second shaft 50 comprising a proximal end (not shown) and a distal end 54 is disposed alongside the elongate body 12 of endoscope 10. The distal end 54 of second shaft 50 extends through, and is slidably and rotationally disposed within, the second lumen 25 of endoscopic hood 20. The first and second shafts 40, 50 may be formed form a sufficiently flexible and torsionally rigid material that permits the shafts to bend and/or flex as the endoscope is advanced and/or retracted through a lumen of a patient, while still being able to translate movement to tissue cutting and tissue engaging elements 48, 58 (discussed below). The second shaft 50 may be secured to the outer surface of the elongate body 12 along the length of the endoscope 10 by one or more clips 62. While the clip 62 of FIG. 2 engages a portion of the outer surface of the elongate body 12, a variety of clip configurations are contemplated by the present disclosure, including, for example, the fully circumferential clip 62 of FIG. 7. The distal end 44 of first shaft 40 may include a tissue cutting element 48. The tissue cutting element 48 may be a mechanical tissue cutting element, including, for example, a knife, blade, scissors or blunt dissector. The tissue cutting element may be an energy-based tissue cutting element, including, for example, RF energy, monopolar DC current, bipolar DC current, ultrasonic energy, laser energy, cryogenic energy or waterjet energy. The distal end 54 of the second shaft 50 may include a tissue engaging element 58, such as, by way of non-limiting example, a grasper, clip, corkscrew, hook or suction device. The tissue cutting element 48 and tissue engaging element 58 of FIG. 2 are depicted in a delivery configuration which minimizes the profile of the endoscopic system to minimize the risk of perforation upon movement through the lumen of a patient. Specifically, the second shaft 50 is rotated such that the tissue engaging element 58 is positioned within the working area 29. The first shaft 40 is retracted within the working channel 18 of the endoscope 10 with the distal end 44 of the first shaft 40 supported within the aperture 31 of the support member 30.

Figure 3A:
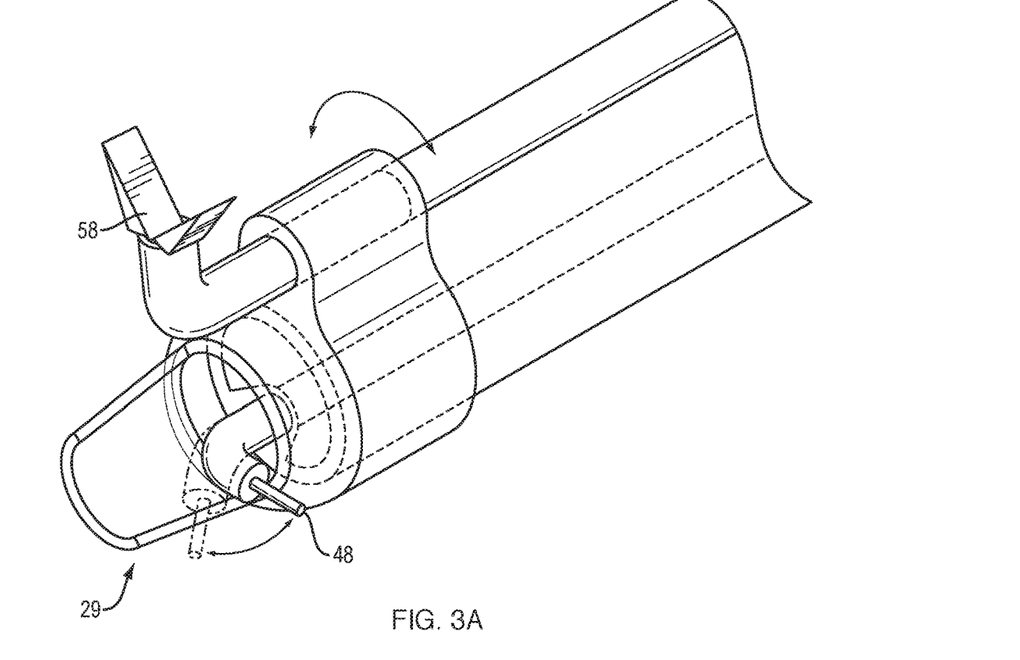
FIGS. 3A-C provide a perspective view of the endoscopic hood and endoscope of FIG. 2 with the tissue cutting element deployed into the working space defined by the endoscopic hood, according to the present disclosure.
Figure 3B:
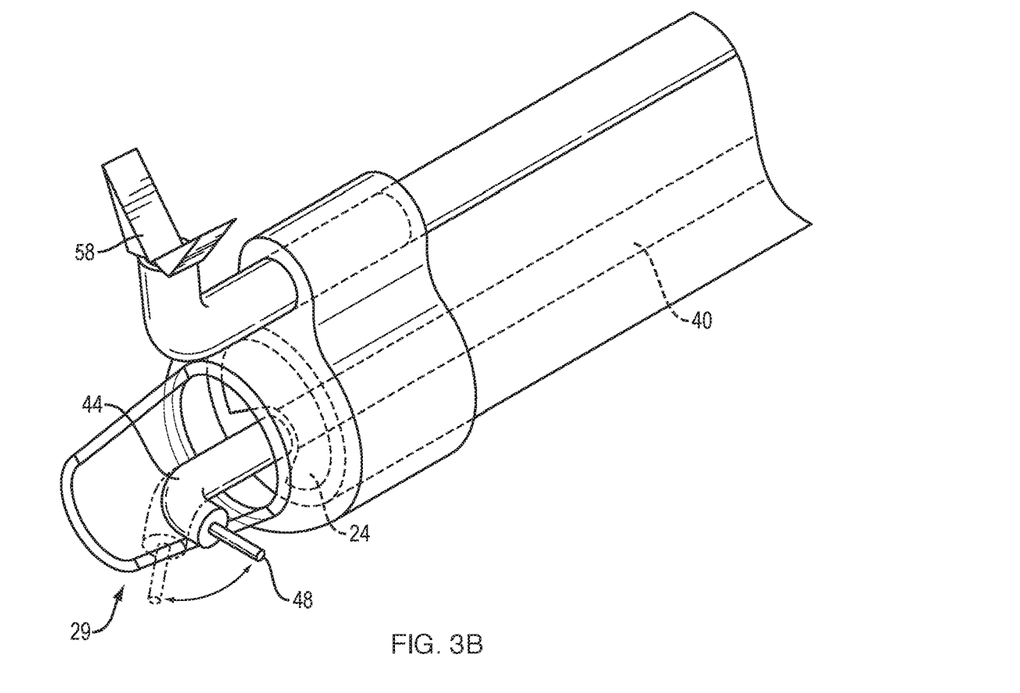
Figure 3C:
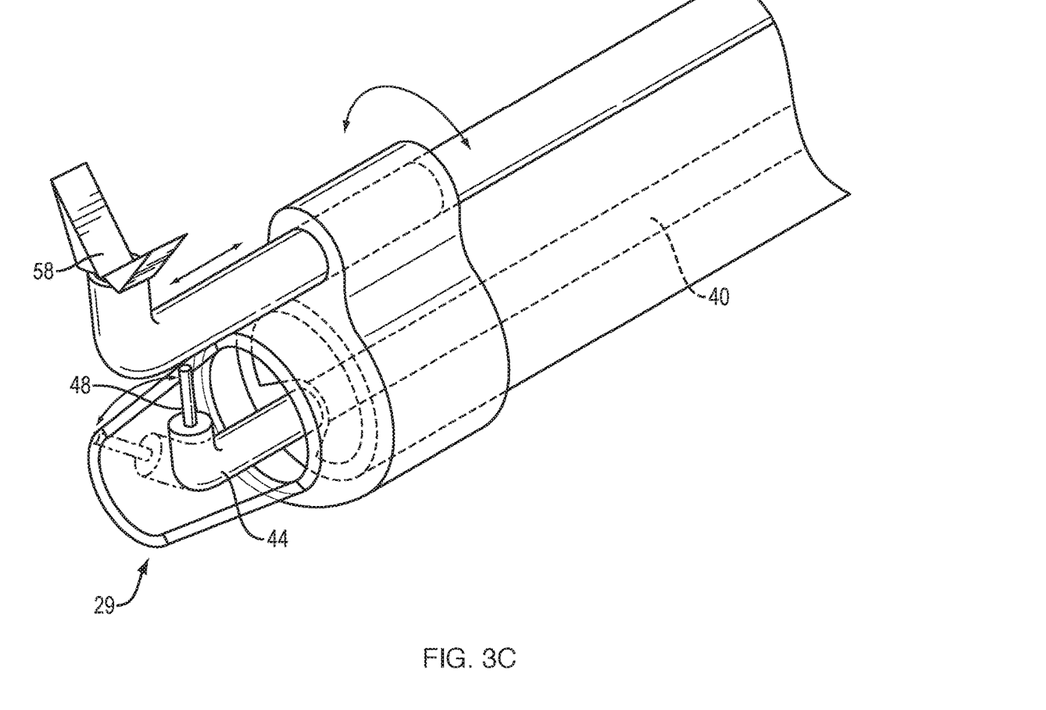

As illustrated in FIGS. 3A-3C, the tissue cutting element 48 and tissue engaging element 58 are configured to operate within the working area 29 on the side of the endoscopic hood, rather than beyond the distal end of the endoscopic hood as with conventional endoscopic hoods. The distal end 44 of the first shaft 40 may include a shape memory material (e.g., nitinol, shape memory polymer, heat-set core wire etc.) that assumes a bent configuration upon advancing through the first lumen 24 into the working area 29. For example, the tissue cutting element 48 may assume a bent configuration having a predetermined angle of approximately 45 degrees to approximately 110 degrees relative to the first shaft 40. The physician may extend (FIG. 3B) and/or retract (FIG. 3A) the first shaft 40 to vary the position of the tissue cutting element 48 within the working area 29. The physician may also extend, retract and rotate the tissue engaging element 58 away from and towards the working area 29 (FIG. 3C). For example, the tissue engaging element 58 may be used to grasp (i.e., engage, grip, hold etc.) tissues using a rotary lifting or descending motion and/or a longitudinal push/pull motion to retract tissue away from, or pull tissue into, the tissue cutting element 48.

As best illustrated in FIGS. 3B and 3C, once extended to the desired location within the working area 29, the tissue cutting element 48 is configured to move in a sweeping (i.e., side-to-side) or poking motion within a single plane. The physician may control the sweeping motion of the tissue cutting element 48 by extending and/or retracting an oversheath (not shown) that retains a portion of the distal end 44 of the first shaft 40. The physician may also control the sweeping motion of the tissue cutting element 48 by actuating (i.e., pushing/pulling) a core wire (not shown) that extends the length of the first shaft 40. The core wire may include a series of pivot points or segments having increased flexibility relative to the remainder of the core wire to facilitate sweeping of the tissue cutting element 48. Additional dexterity in tissue cutting may be achieved by simultaneously advancing or retracting the first shaft 40 while sweeping the tissue cutting element (i.e., left-to-right and/or right-to left). Because actuation of the tissue cutting and tissue engaging elements 48, 58 is not tied to endoscopic tip articulation, the physician may position the endoscope over the tissue region of interest and then control the operation of one (or both) both tools using a single hand.

Figure 4A:
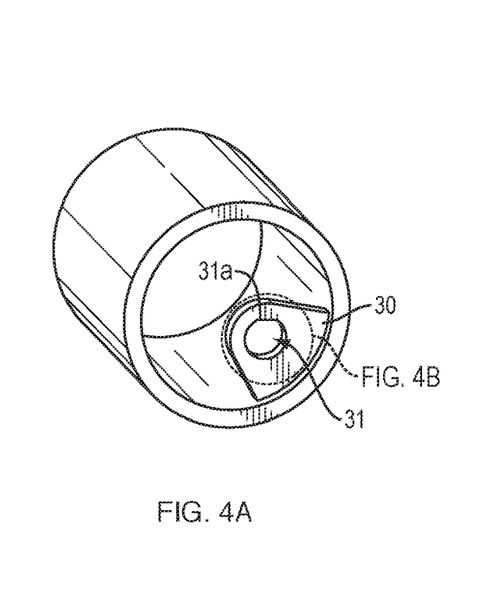
FIGS. 4A-C provide an expanded view of the support member within the lumen of the endoscope hood (FIG. 4A-B) to guide the tissue cutting element (FIG. 4C) within the working space of the endoscopic hood, according to another embodiment of the present disclosure.
Figure 4B:
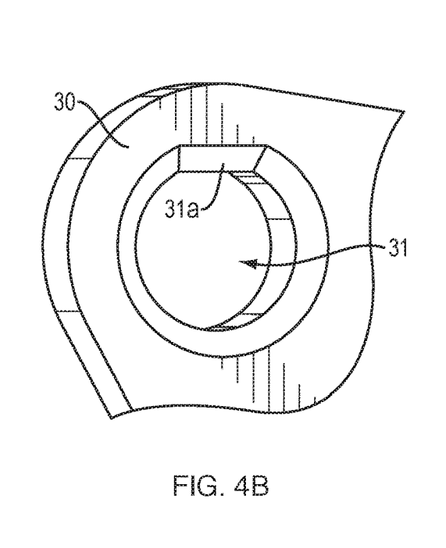
Figure 4C:
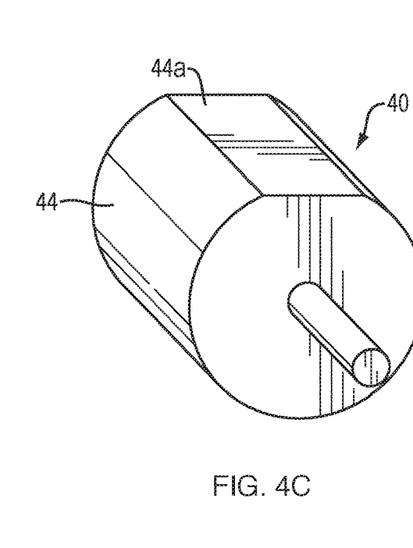
Figure 5A:
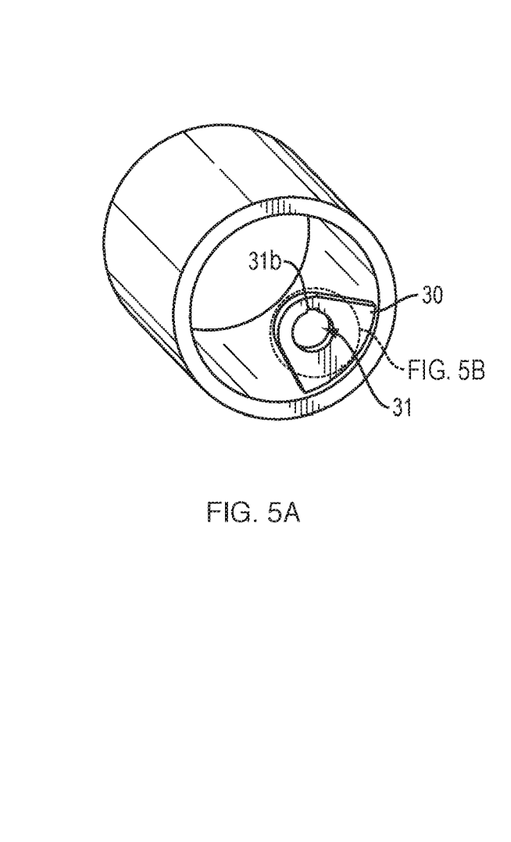
FIGS. 5A-C provide an alternative configuration of the support member and tissue cutting element of FIGS. 4A-C.
Figure 5B:
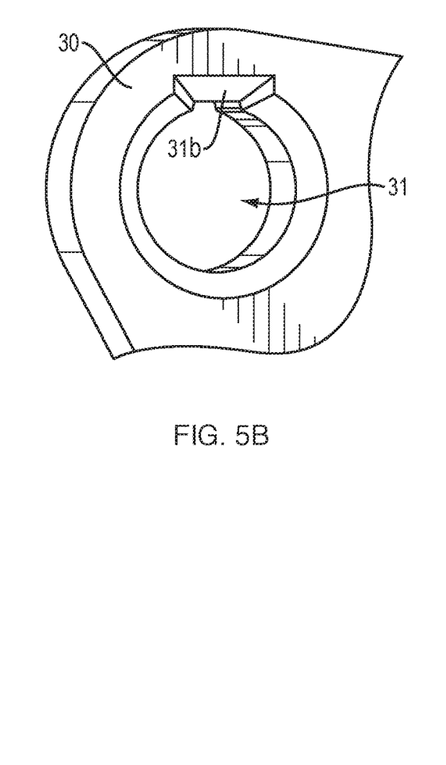
Figure 5C:
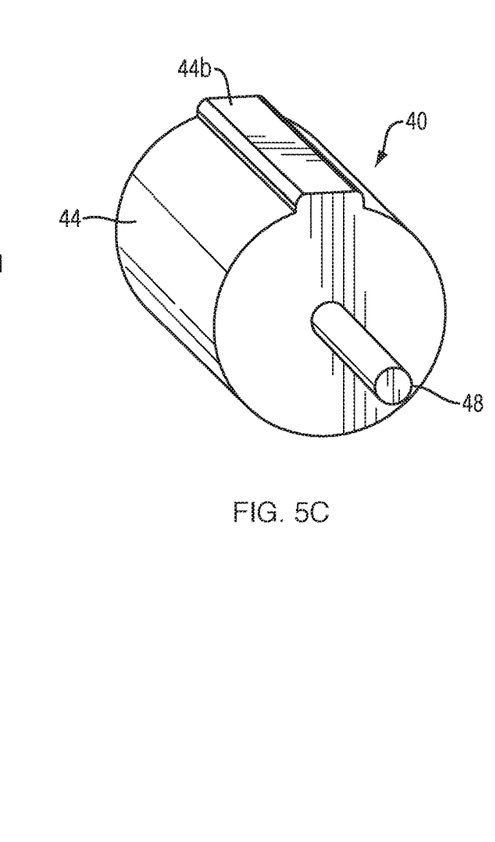

As illustrated in FIGS. 4A-4B, the endoscopic hood may guide the tissue cutting element within the working area using a support member 30 (i.e., alignment channel) that defines an aperture 31 having a non-circular cross-section. For example, the aperture 31 may be of substantially circular cross-section except for a flat portion 31a. Referring to FIG. 4C, the distal end 44 of the first shaft 40 may include a substantially circular cross-section having a corresponding flat portion 44a configured to slide within the aperture 31. As illustrated in FIGS. 5A-5B, the aperture 31 may be of substantially circular cross-section, except for a recessed portion 31b. Referring to FIG. 5C, the distal end 44 of the first shaft 40 may include a substantially circular cross-section having a corresponding raised portion 44b (FIG. 5C) configured to slide within the aperture 31. In either embodiment, the non-circular configuration of the aperture 31 ensures that the tissue cutting element 48 is aligned within working area 29 in a single plane. Unlike conventional devices that guide tools through multiple planes, the endoscopic hood 20 of the present disclosure may provide increased control of tissue manipulation by controlling the tissue cutting element 48 in a single plane.

Figure 6:
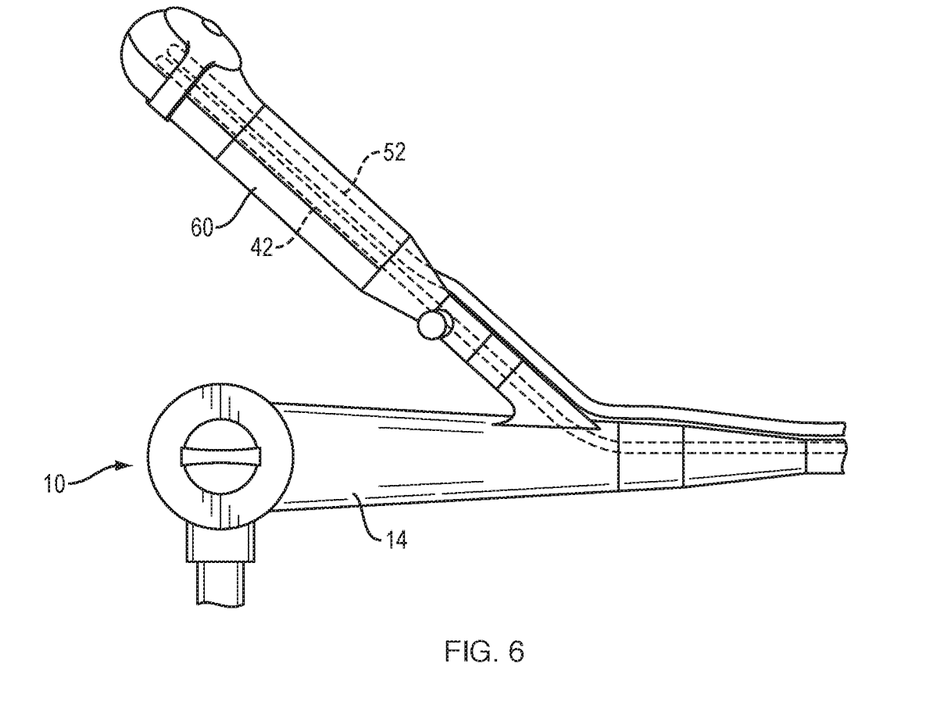
FIG. 6 provides a side view of the control handle attached to the proximal end of the endoscope that allows the physician to manipulate the tissue cutting element and tissue engaging element simultaneously, according to an embodiment of the present disclosure.

The transparent (i.e., clear) wall 27 and large working area 29 of the endoscopic hood 20 provide the physician with a large and unobstructed field of view that is not possible with fully circumferential endoscopic hoods. Referring to FIG. 6, the proximal ends 42, 52 of the first and second shafts 40, 50 may be actuated using a handle 60 at the proximal end 14 of the endoscope 10. The ability of the physician to simultaneously manipulate the tissue cutting element 48 and tissue engaging element 58 using separate motions that require few degrees of motion and which are not tied to endoscope tip articulation allows tissue resection or dissection to be performed with increased speed and precision. Although endoscopic tip articulation is only required for navigating and positioning the tissue cutting element 48 and tissue engaging element 58 over a target tissue, it should be appreciated that the curved shape of the wall 27 of the endoscopic hood 20 may be used to press against tissues as necessary during the medical procedure. For example, the physician may articulate the endoscope such that the curved wall 27 presses against a portion of the tissue, thereby raising and/or exposing another portion of the tissue for grasping and or cutting using the respective tools.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An endoscopic hood configured to be disposed at a distal end of an endoscope comprising an endoscope body and a working channel disposed within the endoscope body, the endoscopic hood comprising:
    a first portion comprising a proximal end, a distal end and first and second lumens extending therebetween;
    a second portion extending from the distal end of the first portion, said second portion comprising a curved wall with an open distal end and defining a working area adjacent a concave surface of the curved wall and the first lumen; and
    a support member extending into the first lumen adjacent to the curved wall;
    wherein the first lumen is configured to receive a portion of a shaft of a first device disposed in the working channel of the endoscope, and wherein the second lumen is configured to slidably and rotationally receive a portion of a shaft of a second device disposed along an outer surface of the endoscope.

2. The endoscopic hood of claim 1, wherein the curved wall comprises one or more of a partial hollow conic section, a partial hollow cylinder or a partial hollow sphere.

3. The endoscopic hood of claim 1, wherein the curved wall comprises a cross-section in the form of an arc.

4. The endoscopic hood of claim 3, wherein the arc ranges from approximately 90 degrees to approximately 180 degrees.

5. The endoscopic hood of claim 1, wherein the curved wall is formed from a transparent material.

6. The endoscopic hood of claim 1, wherein the support member defines an aperture having a non-circular cross-section.

7. An endoscopic system comprising:
   an endoscope comprising an elongate body having a proximal end, a distal end and a working channel disposed within the elongate body;
   an endoscopic hood coupled to the distal end of the endoscope, the endoscopic hood comprising:
      a first portion comprising a proximal end, a distal end and first and second lumens extending therebetween, wherein the first lumen is in communication with the working channel of the endoscope,
      a second portion extending from the distal end of the first portion, said second portion comprising a curved wall with an open distal end and defining a working area adjacent a concave surface of the curved wall and the first lumen, and
      a support member extending into the first lumen adjacent to the curved wall;
   a first shaft having a proximal end and a distal end, wherein a portion of the first shaft is disposed within the working channel and the first lumen; and
   a second shaft having a proximal end and a distal end, wherein a portion of the second shaft is slidably and rotationally disposed along an outer surface of the elongate body and extends through the second lumen.

8. The endoscopic system of claim 7, wherein the curved wall comprises one or more of a partial hollow conic section, a partial hollow cylinder or a partial hollow sphere.

9. The endoscopic system of claim 7, wherein the curved wall comprises a cross-section in the form of an arc.

10. The endoscopic system of claim 7, wherein the support member defines an aperture having a non-circular cross-section.

11. The endoscopic system of claim 10, wherein the aperture of the support member is configured to slidably receive the first shaft.

12. The endoscopic system of claim 7, wherein the first shaft is slidably, but not rotationally, disposed within the working channel and first lumen.

13. The endoscopic system of claim 7, wherein the distal end of the first shaft includes a shape memory material that is configured to assume a bent configuration when unconstrained by an over-sheath or core wire.

14. The endoscopic system of claim 7, wherein the distal end of the first shaft includes a tissue cutting element, and wherein the distal end of the second shaft includes a tissue engaging element.

15. The endoscopic system of claim 14, wherein rotating a proximal end of the second shaft in a first direction moves the tissue engaging element towards the working area, and rotating a proximal end of the second shaft in a second direction moves the tissue engaging element away from the working area.

16. The endoscopic system of claim 14, wherein the tissue cutting element is configured to bend upon actuation by an operation.

17. The endoscopic system of claim 7, wherein the curved wall comprises a cross-section in the form of an arc.

18. The endoscopic system of claim 17, wherein the arc ranges from approximately 90 degrees to approximately 180 degrees.

19. The endoscopic system of claim 7, wherein the curved wall is formed from a transparent material.

20. A method of resecting or dissecting tissue, comprising:
   a) inserting, into a body lumen of a patient, an endoscopic system comprising:
      an endoscope comprising an elongate body having a proximal end and a distal end and a working channel disposed within the elongate body;
      an endoscopic hood coupled to the distal end of the endoscope, the endoscopic hood comprising:
         a first portion comprising a proximal end, a distal end and first and second lumens extending therebetween, wherein the first lumen is in communication with the working channel of the endoscope; and
         a second portion extending from the distal end of the first portion, said second portion comprising a curved wall with an open distal end and defining a working area adjacent a concave surface of the curved wall and the first lumen;
      a first shaft having a proximal end and a distal end, wherein a portion of the first shaft is disposed within the working channel and the first lumen; and
      a second shaft having a proximal end and a distal end, wherein a portion of the second shaft is slidably and rotationally disposed along an outer surface of the elongate body and extends through the second lumen, wherein the distal end of the first shaft includes a tissue cutting element, and wherein the distal end of the second shaft includes a tissue engaging element;
   b) positioning the endoscopic hood over the surface of a target tissue; and
   c) resecting or dissecting the target tissue with said tissue cutting element while engaging the tissue with said tissue engaging element.

* * * * *